(12) United States Patent
Boettcher et al.

(10) Patent No.: US 10,232,331 B2
(45) Date of Patent: Mar. 19, 2019

(54) SYSTEM AND METHOD FOR RECEIVING A SINGLE-USE VESSEL

(71) Applicant: Sartorius Stedim Biotech GmbH, Goettingen (DE)

(72) Inventors: Lars Boettcher, Melsungen (DE); Jonathan E. Cutting, East Setuaket, NY (US); Sharon D. West, Sunnyside, NY (US); Martin Oschwald, Tagelswangen (CH)

(73) Assignee: Sartorius Stedim Biotech GmbH (DE)

( * ) Notice: Subject to any disclaimer, the term of this patent is extended or adjusted under 35 U.S.C. 154(b) by 328 days.

(21) Appl. No.: 15/010,356

(22) Filed: Jan. 29, 2016

(65) Prior Publication Data
US 2017/0216799 A1 Aug. 3, 2017

(51) Int. Cl.
| | |
|---|---|
| *B23Q 1/00* | (2006.01) |
| *B01F 7/22* | (2006.01) |
| *B01F 15/00* | (2006.01) |
| *B65D 25/20* | (2006.01) |
| *C12M 1/00* | (2006.01) |
| *C12M 1/06* | (2006.01) |
| *G06K 7/10* | (2006.01) |
| *B01F 7/16* | (2006.01) |
| *B01F 13/00* | (2006.01) |

(52) U.S. Cl.
CPC ........ *B01F 15/00318* (2013.01); *B01F 7/162* (2013.01); *B01F 7/163* (2013.01); *B01F 7/1695* (2013.01); *B01F 7/22* (2013.01); *B01F 13/004* (2013.01); *B01F 13/0042* (2013.01); *B01F 15/0085* (2013.01); *B01F 15/00857* (2013.01); *B65D 25/205* (2013.01); *C12M 23/14* (2013.01); *C12M 23/26* (2013.01); *C12M 23/28* (2013.01); *C12M 27/02* (2013.01); *G06K 7/10366* (2013.01); *B01F 2015/00584* (2013.01); *B01F 2015/00597* (2013.01); *B01F 2215/0073* (2013.01)

(58) Field of Classification Search
CPC ........... B01F 7/22; B01F 15/0085; B23Q 1/00
USPC ...................................................... 366/142
See application file for complete search history.

(56) References Cited

U.S. PATENT DOCUMENTS

| | | | | |
|---|---|---|---|---|
| 5,431,201 | A * | 7/1995 | Torchia | A61J 1/20 141/100 |
| 2015/0210012 | A1 * | 7/2015 | Zenere | B01F 13/0818 425/162 |

\* cited by examiner

*Primary Examiner* — David L Sorkin
(74) *Attorney, Agent, or Firm* — Gerald E. Hespos; Michael J. Porco; Matthew T. Hespos

(57) ABSTRACT

A system for receiving a single-use vessel containing a mixing device has a support structure adapted to receive the single-use vessel and a drive-unit adapted to power, to control, or to power and control a mixing of contents of the single-use vessel when the single-use vessel is arranged in the support structure. The support structure and the drive-unit are provided as separate components that may be arranged both in an operating position, where the drive-unit is connectable to the mixing device of the single-use bag in the support structure, and in a separated position, where the drive-unit is separated from the support structure. The drive-unit comprises a tag reader that, in the operating position, is arranged to read a vessel tag of the single-use vessel arranged in the support structure.

16 Claims, 5 Drawing Sheets

SYSTEM AND METHOD FOR RECEIVING A SINGLE-USE VESSEL

BACKGROUND

1. Field of the Invention

The invention relates to a system for receiving a single-use vessel and a method for receiving a single-use vessel.

2. Related Art

Single-use systems, i.e. bioreactors and/or pallettanks, are becoming increasingly prevalent in the biopharmaceutical industry because of flexibility, reduced capital cost, reduced risk of cross-contamination, and utility savings compared to traditional stainless steel systems. Single-use vessels, i.e. containers and/or bags, are commonly made of flexible multilayer film and, as a consequence, may require a support structure, i.e. a box, to prevent sagging and rupture due to hydrostatic pressure when filled with liquid. The support structure is suitable to receive the single-use vessel. In the support structure, the single-use vessel may be tempered for a predetermined time. Furthermore, the contents of the single-use vessel may be mixed and/or examined within the support structure. Such "bag-in-box" systems are already available from several suppliers (e.g. Sartorius, Pall, Millipore, Thermo Scientific).

Some applications require that a mixing equipment is fully closed with no possibility of leakage between the mixing vessel and the environment—for example, the fluids to be mixed may be either hazardous (e.g. toxic) or sensitive to contamination from the outside environment (e.g. highly purified pharmaceutical material). In such cases, a magnet drive system may be employed as a means of transmitting torque between an external motor and a mixing device (e.g. an impeller) arranged inside of the single-use vessel.

The system may further comprise a drive-unit containing the external motor and/or a related control system. The drive-system may be provided as a separate component of the system that can engage with the supporting structure. This arrangement allows sharing one drive-unit across many different support structures, thereby reducing the capital cost.

It is a problem to improve engaging the drive-unit to the supporting structure and/or the single-use vessel.

SUMMARY

A first aspect of this disclosure relates to a system for receiving a single-use vessel containing a mixing device. The system comprises a support structure adapted to receive the single-use vessel. The system further comprises a drive-unit adapted to power and/or control a mixing of contents of the single-use vessel when the single-use vessel is arranged in the support structure. The support structure and the drive-unit are provided as separate components of the system that may be arranged both in an operating position where the drive-unit is connectable to the mixing device of the single-use bag in the support structure, and in a separated position where the drive-unit is separated from the support structure. The drive-unit comprises a tag reader that, in the operating position, is arranged to read a vessel tag of the single-use vessel arranged in the support structure.

The system may be adapted to receive, temper, store, mix, and/or examine contents of the single-use vessel. Thus, the single-use vessel may be exchangeable.

The single-use vessel that the system is adapted to receive may be provided as a single-use container and/or a single-use bag made of a flexible multilayer film. The single-use vessel may be aseptic. The single-use vessel may comprise a mixing device adapted to mix the contents of the single-use vessel when powered from the drive-unit. The mixing device may comprise an impeller that is connectable to the drive-unit.

The system comprises at least two components, namely the support structure and the drive-unit. These two components may become completely separated from each other in the separated position. In particular, the drive-unit may be adapted to be connected to other, e.g. different, support structure(s). In the operating position, the drive-unit may be coupled to the support structure, e.g. in a fixed position relative to the support structure. The drive-unit may comprise a motor and/or a controller. The motor of the drive-unit may be coupled to the mixing device of the single-use vessel when the system is in the operating position and the single-use vessel is arranged in the support structure.

The support structure may be provided as a mechanical support structure and may comprise a rigid box that may prevent sagging and/or rupture of the single-use vessel due to hydrostatic pressure when filled with liquid.

The drive-unit comprises the tag reader that may face the single-use vessel inside the support structure. The single-use vessel may be provided with a vessel tag associated to tag information that may be accessible by the drive-unit after reading and/or scanning the vessel tag. A coupling of the drive-unit to the mixing device of the single-use vessel, and also a mixing sequence of contents of the single-use vessel driven by the drive-unit, may depend on the tag information associated to the vessel tag. Thus, a coupling and engaging of the drive-unit to the support structure may be improved.

The tag reader may be arranged at a fixed position on the drive-unit and may be arranged to face the support structure in the operating position. In an alternative embodiment, the tag reader may be implemented as a hand-held tag reader that may be pointed at the vessel tag by an operator.

A second aspect of this disclosure relates to a method for receiving a single-use vessel containing a mixing device, comprising the steps:

providing a single-use vessel comprising a vessel tag,
arranging the single-use vessel in a support structure,
arranging a drive-unit in an operating position relative to the support structure, so that a tag reader of the drive-unit is arranged to read the vessel tag,
reading the vessel tag of the single-use vessel by the tag reader,
processing tag information associated to the vessel tag,
connecting the drive-unit to the mixing device of the single-use vessel to power and/or control a mixing of contents of the single-use vessel.

The method may be performed in a system according to the first aspect.

A third aspect of the disclosure relates to a single-use vessel containing a mixing device and comprising a vessel tag at a position facing substantially outwards. The single-use vessel is adapted to be received by a support structure of a system such that the vessel tag is arranged to be read by a tag reader of the system. The single-use vessel may, e.g., be arranged in the support structure of the system according to the first aspect. The single-use vessel may also be used in the method according to the second aspect.

The following paragraphs describe exemplary embodiments that may be combined with each other to form further embodiments.

The support structure may comprise positioning means adapted to position and/or receive the single-use vessel so that the vessel tag of the single-use vessel is arranged in a designated reading area of the support structure. This may be achieved by arranging the tag vessel at a predetermined position on the single-use vessel and/or by arranging the single-use vessel in a predetermined position within the supporting structure. The reading area may be implemented and provided to allow a tag reader to read any tag that is arranged within the reading area. In particular, the reading area may be transparent. The positioning means may comprise mounting structures like a hook, a screw, a spring, a latch, etc.

The reading area of the support structure may comprise a window substantially facing the drive-unit in the operating position. The window may be implemented as an opening in the support structure. The opening may be freely accessible gap or covered by a transparent material such as glass and/or plastic. A closed window may improve the aseptic integrity of the system. An optical window may improve a readability of the vessel tag while keeping the aseptic integrity.

The tag reader of the drive-unit may substantially face the reading area of the support structure in the operating position. Thus, the tag reader is enabled to read the vessel tag whenever the drive-unit is arranged in the operating position without needing an operator to manually operate the tag reader.

In an embodiment, the support structure comprises a structure tag arranged to be readable by the tag reader when the drive-unit is in the operating position. For example, the structure tag may be arranged in vicinity of the reading area so that both the vessel tag and the structure tag may be read by the tag reader arranged at a fixed position on the drive-unit.

In an embodiment, the structure tag of the support structure is associated to tag information regarding at least one of the following:
 a product code,
 a product type,
 a serial number,
 an intended vessel volume,
 compatible ports,
 compatible lines,
 portable or fixed,
 a manufacturing date, and/or
 manufacturer test results.

Thus, a controller of the drive-unit may access tag information associated with the support structure and/or the single-use vessels the support structure is adapted to receive, temper, mix, examine, etc. The tag information may be stored in the structure tag and/or in a database associated to the structure tag. The controller of the drive-unit may have access to such a database.

In an embodiment, the tag reader is adapted to determine, from the vessel tag of the single-use vessel, tag information regarding at least one of the following:
 a product code,
 a product type,
 a serial number,
 a lot number,
 a vessel volume,
 ports of the single-use vessel,
 lines of the single-use vessel,
 a sensor feature,
 a sensor calibration information,
 characteristics of the mixing device, in particular impeller characteristics,
 a manufacturing date,
 content of the vessel,
 an irradiation date,
 an expiration date, and/or
 manufacturer test results Thus, a controller of the drive-unit may access tag information associated with the single-use vessel. The tag information may be stored in the vessel tag and/or in a database associated to the vessel tag. The controller of the drive-unit may have access to such a database.

In an embodiment, the tag reader is adapted to read a QR code and/or an RFID tag. Therein, the vessel tag and/or the structure tag may be implemented as QR code and/or as RFID tag. Preferably, the vessel tag and/or the structure tag is implemented as a 2-dimensional code like a QR code.

In an embodiment, the system further comprises a controller connected to the tag reader that is adapted to receive tag signals from the tag reader and that is further adapted to process said tag signals, thereby extracting tag information associated to the vessel tag and/or to a structure tag of the support structure. The tag information may be stored in the vessel/structure tag and/or in a database associated to the vessel/structure tag. The controller of the drive-unit may have access to such this database. The controller may comprise a processor like a computer processor.

In a further development of this embodiment, the controller of the drive-unit is adapted to control the drive-unit depending on the extracted tag information. This may include a mixing program, a rotation direction, a temperature, a time period, a duration, and/or a rotation speed that depends on the tag information.

In an embodiment, the drive-unit is arranged below the single-use bag in the operating position. Thus, at least a part of the support structure, in particular the part of the support structure in which the single-use vessel may be received, may be arranged above the drive-unit in the operating position.

In this disclosure, terms as "above", "below", "bottom side", "upper side", etc. refer to the reference system of the Earth.

According to an embodiment, the drive-unit is mounted on rolls. Thus, the drive-unit may be easily moved to and from the support structure.

According to an embodiment of the second aspect, the drive-unit powers and/or controls the mixing of the contents of the single-use vessel depending on the processed tag information. This may include a mixing program, a rotation direction, a temperature, a time period, a duration, and/or a rotation speed that depends on the tag information.

According to an embodiment, before the drive-unit is connected to the mixing device of the single-use vessel, it is confirmed based on the processed tag information that the drive-unit and/or the support structure is/are compatible with the single-use vessel. In case an incompatibility is established, the drive-unit is not connected to the single-use vessel. Instead, an error may be indicated.

The invention is further illustrated in reference to embodiments shown in the figures. Embodiments of the invention are described with reference to the figures. Features of the embodiments shown in the figures may be combined with alternative embodiments. Reference numbers identify identical or similar features of different embodiments.

DETAILED DESCRIPTION

Figure 1A:
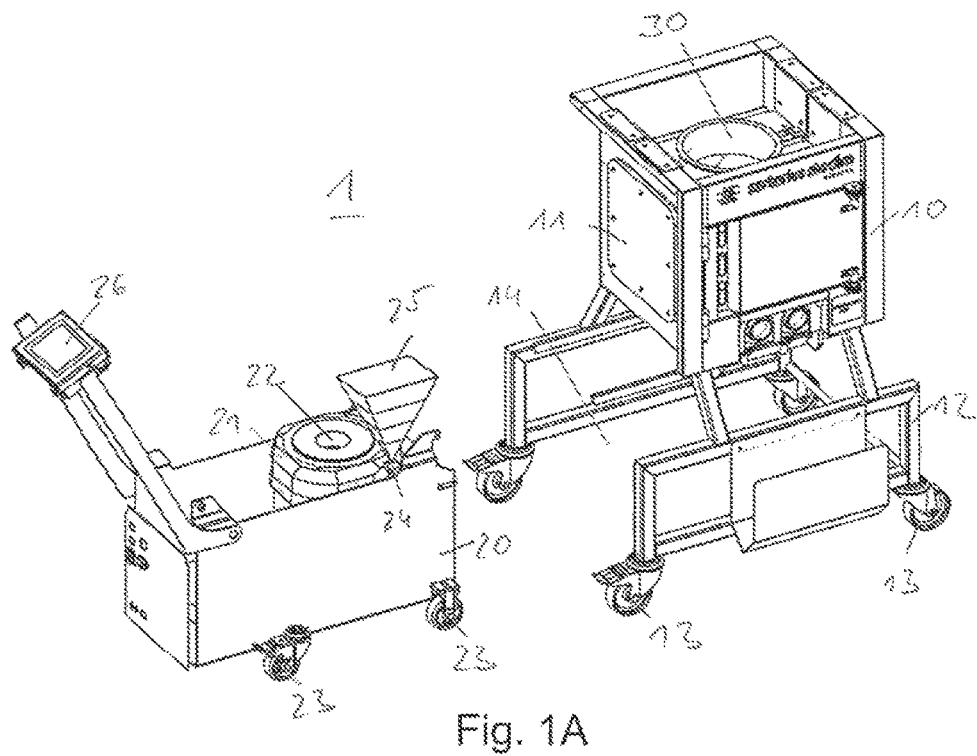
FIG. 1A a perspective view of a system for receiving a single-use vessel in a separated position.
Figure 1B:
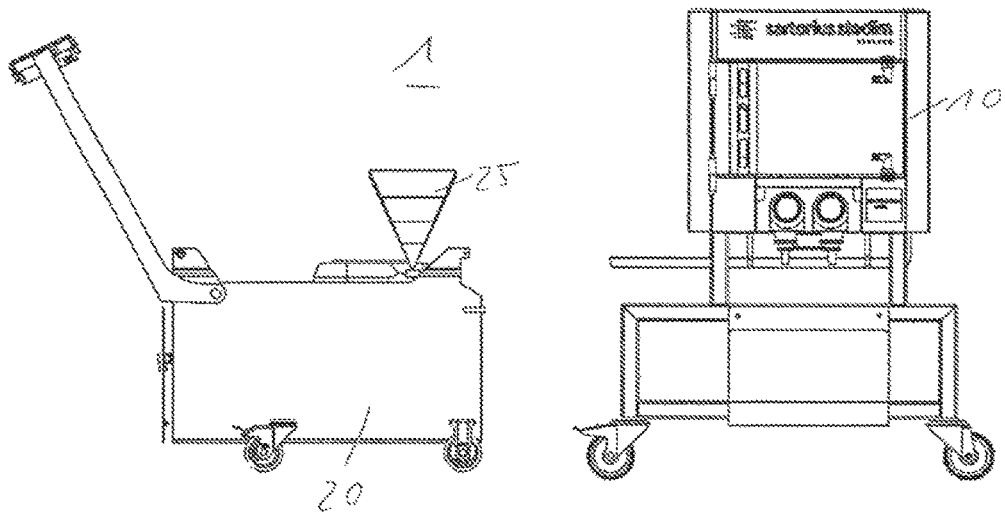
FIG. 1B a side view of the system for receiving a single-use vessel in a separated position.

FIGS. 1A and 1B show a system 1 for receiving a single-use vessel in a perspective view and in a side view. The system 1 comprises a support structure 10 and a drive-unit 20. These two components of the system 1 are arranged separated from each other in a separated position wherein the drive-unit 20 is arranged separated from the support structure 10. The system 1 may be provided as a single-use systems, i.e. as a bioreactors and/or as a pallettank for the biopharmaceutical industry. The system 1 is suitable to receive the single-use vessel and/or to temper, mix and/or examine the contents of the single-use vessel.

The support structure 10 comprises a stand 12 mounted on rolls 13 that may enable an easy relocation of the support structure 10. In an alternative embodiment, the support structure may be provided without any rolls comprising a fixed and static stand.

The stand 12 comprises a frame supporting a receiving section 11 of the support structure 10. The receiving section 11 may comprise or be implemented as a box-shaped container for receiving a single-use vessel 30. The receiving section 11 is provided as a rigid structure that is adapted to support even a flexible single-use vessel.

The receiving section 11 of the support structure 10 is arranged above the stand 12. Below the receiving section 11, in particular directly below the receiving section 11, the supporting structure 11 comprises a couple section 14. The couple section 14 comprises free space within the stand 12 below the receiving section 11. The couple section 14 comprises at least enough free space to allow the drive-unit 20 to be arranged at least partially within the free space of the couple section 14.

The stand 12 may comprise at least one open side that allows moving the drive-unit 20 within the couple section 14 from said open side.

The support structure 10 may further comprise positioning means to position the single-use vessel 30 in a predetermined position within the receiving section 11. Furthermore, the support structure 10 may comprise guiding means like rails arranged in the stand 12 to guide the drive-unit 20 into the couple section 14. The support structure 10 may also comprise connecting means to connect the drive-unit 20 to the support structure 10 in the operating position of the system 1. The support structure 10 may also comprise at least one port and/or at least one line that may be connected to the single-use vessel 30 within the receiving section 11.

The drive-unit 20 is mounted on rolls 23 that enable simple movement of the drive-unit 20. Furthermore, the drive-unit 20 comprises a motor 21 and a connector 22 arranged so that the connector 22 may be connected and/or coupled to a mixing device of the single-use vessel 30. The motor 21 is coupled to the connector 22. The connector 22 is suitable to couple force from the motor 21 to the mixing device of the single-use vessel 30. Thus, the motor 21 may power, drive, and/or control a mixing of the contents of the single-use vessel 30 as long as the connector 22 is coupled to the mixing device.

The drive-unit 20 comprises a user interface 26 that may be implemented a computer screen, a touch screen, or the like. The user interface 26 may be used to display a status of the system 1, including a compatibility, a mixing sequence, a time, etc. The user interface 26 also be coupled to a controller of the drive-unit 20. An operator may interact with the user interface 26.

Figure 2A:
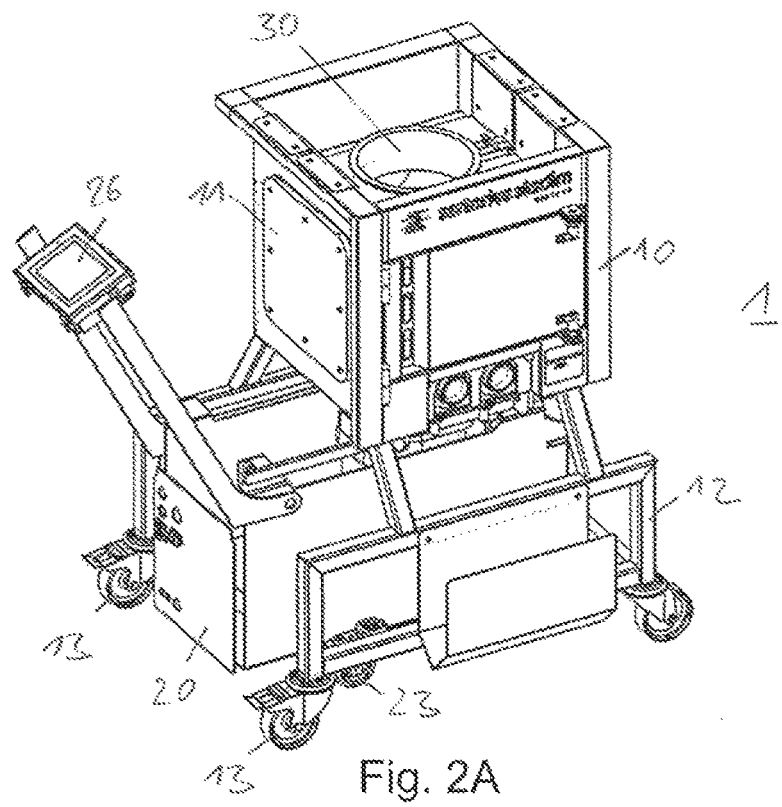
FIG. 2A a first perspective view of the system for receiving a single-use vessel in a operating position.
Figure 2B:
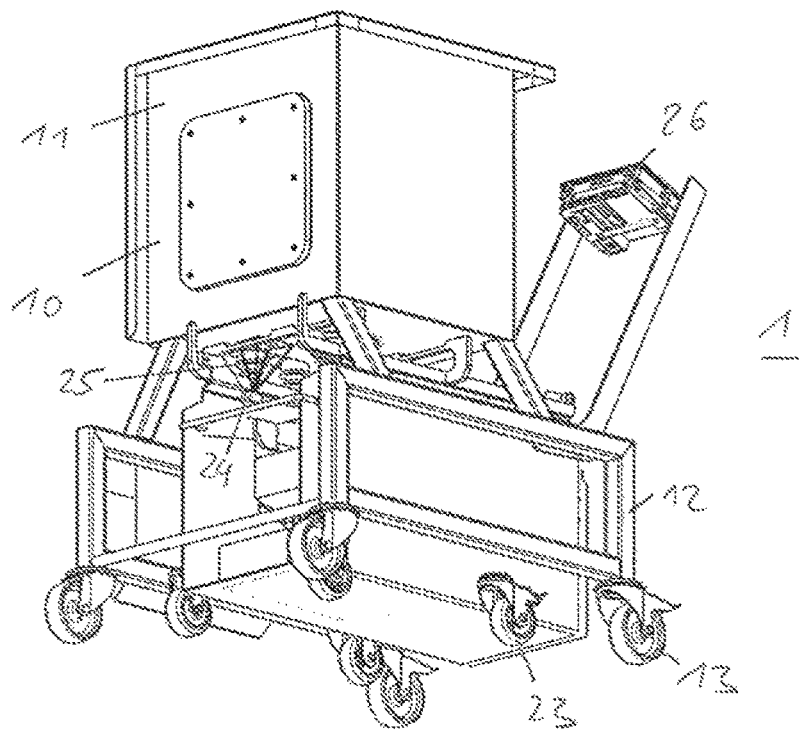
FIG. 2B a second perspective view of the system for receiving a single-use vessel in a operating position.

The drive-unit 20 comprises a tag reader 24 that may be implemented as a scanner. The tag reader 24 is adapted to scan tags within its corresponding scan field 25 that is shown stylised and schematically in FIGS. 1A and 1B as a cone shaped scan field 25. The tag reader 24 is arranged such that its scan field 25 is directed away from the drive-unit 20. In the shown embodiment, the scan field 25 faces in a substantially upwards direction. Generally, the scan field 25 may be arranged so that it faces substantially towards the receiving section 11 of the support structure 10 when the system 1 is in its operating position as shown in FIGS. 2A and 2B referred to below. The scan field 25 may be arranged so that it is substantially parallel to a transmitting direction in which a driving power, e.g. a torque, is transmitted from the motor 21 via the connector 22 to the mixing device of the single-use vessel 30. Thus, the tag reader 24 may be arranged in vicinity of the connector 22.

In the system 1, the drive-unit 20 may be separated from the support structure 10 to be also connected to other support structures.

FIGS. 2A and 2B show two different perspective views of the system 1 in its operating position. In the operating position, the drive-unit 20 is arranged at least partially within the couple section 14 of the support structure 10. At least the part comprising the connector 22 and the tag reader 24 are arranged in the couple section 14 of the support structure 10. In the system 1 shown as embodiment, substantially the whole drive-unit 20 is arranged in the couple section 14 except the user interface 26 and adjacent mounting structures.

As shown in FIG. 2B, in the operating position, the tag reader 24 is arranged such that its scan field 25 is directed substantially towards the receiving section 11 of the support structure 10, e.g. upwards to a bottom side of the receiving section 11. In other words, the scan field 25 is directed towards the single-use vessel 30 when the system 1 is in its operating position and when the vessel 30 is arranged in its predetermined position within the support structure 10.

To move the system 1 from its separated position (shown in FIG. 1A and FIG. 1B) into its operating position (shown in FIG. 2A and FIG. 2B) and backwards, either the drive-unit 20 is moved on its rolls 23, or the support structure 10 is moved on its rolls 13, or both. The drive-unit 20 may be lashed, fixed, coupled, and/or connected to the support structure 10, e.g. by corresponding coupling means.

Figure 3:
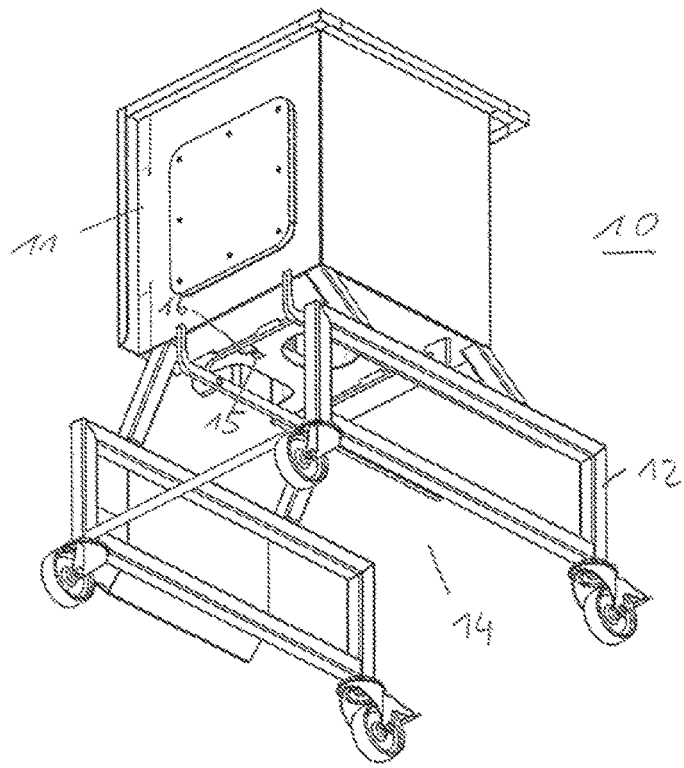
FIG. 3 a perspective view of a support structure of the system for receiving a single-use vessel.

FIG. 3 shows a perspective view of the support structure 10 of the system 1 for receiving a single-use vessel 30. In a section of the receiving section 11 that is facing the drive-unit 20 in the operating position, e.g. in a bottom section of the receiving section 11, the receiving section 11 comprises a reading area 16. The reading area 16 may be implemented or comprise an opening, e.g. a transparent window, an optical window, or a gap. The reading area 16 is arranged within the scan field 25 of the tag reader 24 when the system 1 is in its operating position. The reading area 16 allows the tag reader 24 to read a vessel tag arranged behind the reading area and within the receiving section 11 of the support structure 10. In other words, the reading area 16 allows a view into a section of the receiving section 11.

The support structure 10 further comprises a structure tag 15. The structure tag 15 may be arranged in a section of the receiving section 11 that is facing the drive-unit 20 in the operating position, e.g. in a bottom section of the receiving section 11. The structure tag 15 may be arranged within the scan field 25 of the tag reader 24 when the system 1 is in its operating position. The structure tag 15 may be arranged in vicinity of the reading area 16, in particular no further away than 10 cm, preferably within 5 cm of the reading area 16.

Figure 4A:
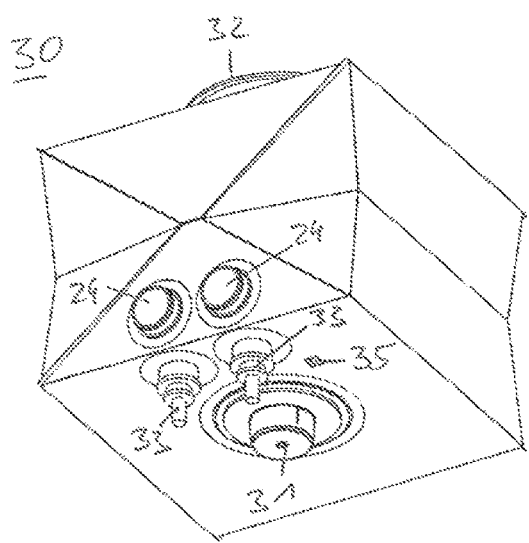
FIG. 4A a first perspective view of a single-use vessel adapted to be received in the system.
Figure 4B:
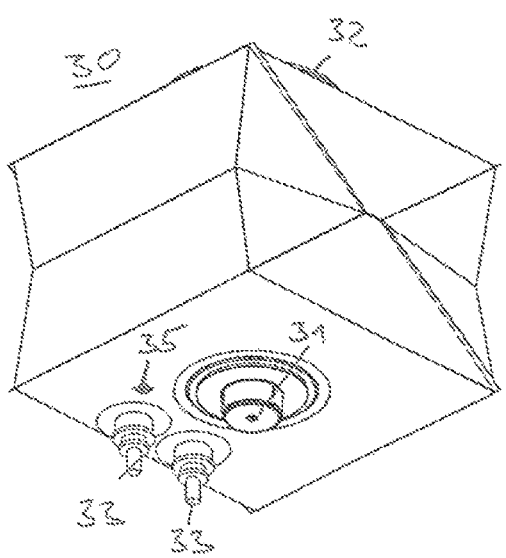
FIG. 4B a second perspective view of the single-use vessel adapted to be received in the system.

FIGS. 4A and 4B show two perspective views of the single-use vessel 30 that is adapted to be received in the system 1. The single-use vessel 30 may be provided as a separate element that may or may not be an element of the system 1. In a preferred embodiment, the single-use vessel 30 is no part of the system 1, but may be arranged within the supporting structure 10 as an exchangeable component.

The single-use vessel 30 may be implemented as a flexible bag. The use of such single-use vessels increases flexibility, reduces capital cost, reduces a risk of cross-contamination, and saves utilities compared to traditional stainless steel systems. The single-use vessel 30 may be made of a flexible multilayer film.

In an inflated condition as shown in FIGS. 4A and 4B, the single-use vessel 30 may resemble a cuboid. In one side of the single-use vessel 30, i.e. a bottom side, the single-use vessel 30 comprises both a mixing device 31 and a vessel tag 35. In an alternative embodiment, the vessel tag 35 and the mixing device 31 may be arranged at different sides of the single-use vessel 30.

The mixing device 31 is connectable to a motor that may power the mixing device 31. In particular, the mixing device 31 may be connectable to the connector 22 of the drive-unit 20 such that the motor 21 of the drive-unit 20 may power, drive, and/or control a mixing of the contents of the single-use vessel 30. The mixing device 31 may comprise an impeller arranged within the single-use vessel 30 and adapter means to connect the mixing device 31 to the connector 22.

The vessel tag 35 may be implemented as 2D barcode, in particular as a QR code (quick response code). The vessel tag 35 may also be implemented as an RFID tag. The vessel tag 35 is arranged at predetermined position relative to the mixing device 31 such that the vessel tag 35 will always be arranged at a predetermined position within the support structure 10. In particular, the vessel tag 35 is arranged in a position such that the vessel tag 35 will be arranged within and/or behind the reading area 16 of the receiving section 11.

The single-use vessel 30 may further comprise a powder port 32, one or more sensors 34, and one or more liquid ports 33. The single-use vessel 30 may be arranged within the receiving section 11 of the support structure 10 such that one or more of its components are connectable with corresponding elements of the system 1, e.g. the mixing device 31 (as referred to above), the powder port 32, the liquid ports(s) 33, the sensor(s) 34, and/or the vessel tag 35.

Figure 5A:
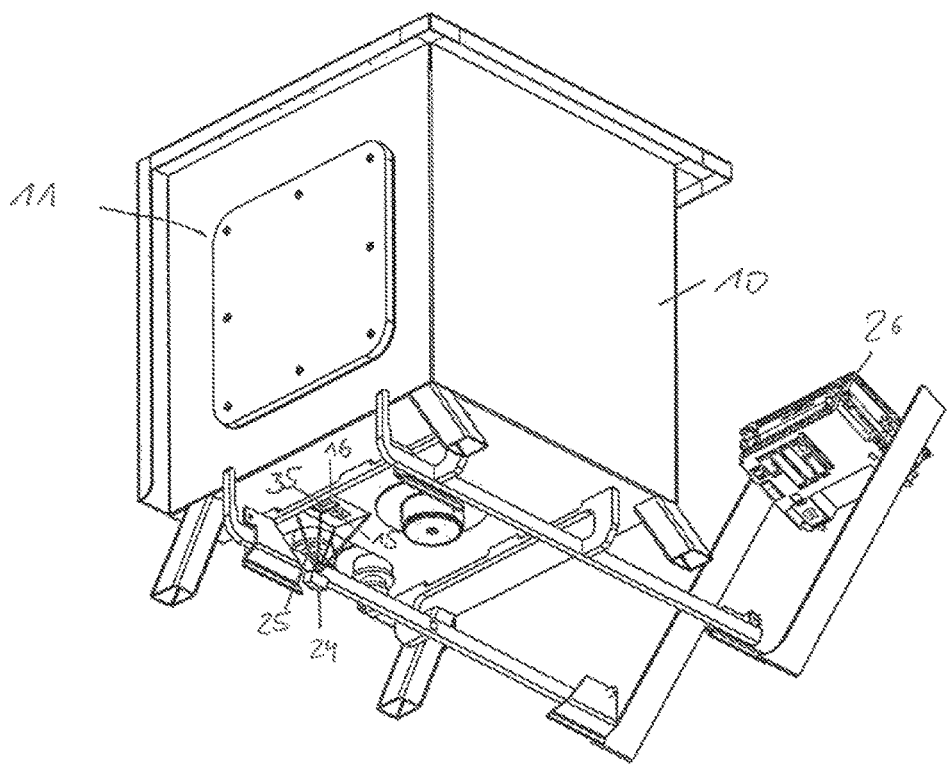
FIG. 5A a perspective view of a part of the system in which the single-use vessel is arranged.
Figure 5B:
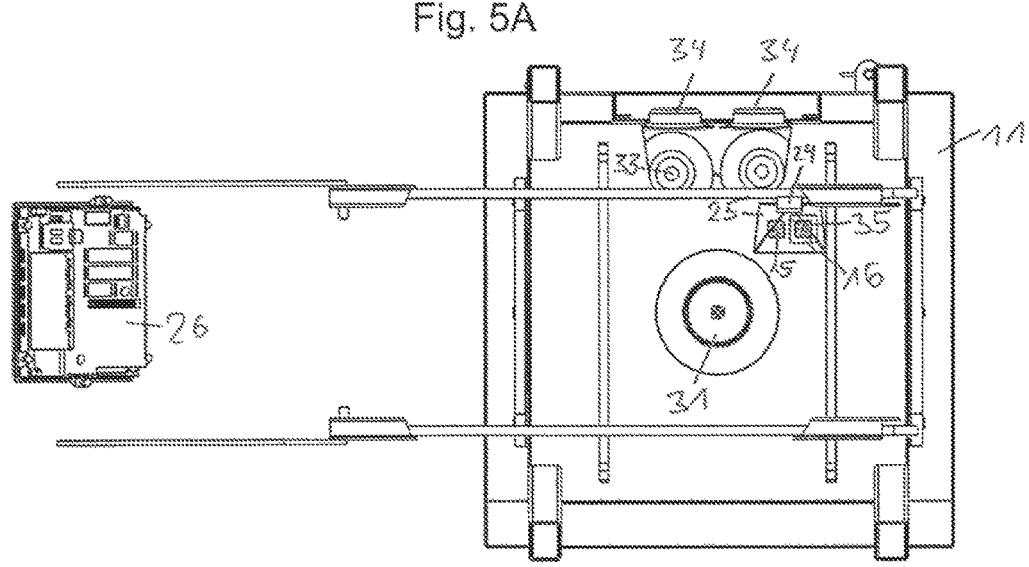
FIG. 5B a bottom view of a part of the system in which the single-use vessel is arranged.

FIGS. 5A and 5B show a perspective view and a bottom view of a part of the system 1 in which the single-use vessel 30 is arranged. In the FIGS. 5A and 5B, most elements of the drive-unit 20 and some elements of the support structure 10 are omitted. The figures show the tag reader 24 and its scan field 25. Within the scan field 25 are arranged the structure tag 15, the reading area 16, and, within said reading area 16, the vessel 35 are clearly visible such that both tags 15 and 35 may be read by the tag reader 24.

The system 1 may comprise a sophisticated controller and/or control system which has the ability to enforce predetermined process rules and guide an operator through a sequence of operations. Therefore, it is advantageous for the controller to have and/or rely on detailed information about the single-use vessel 30 and/or the support structure 10.

The use of information tags such as barcodes or RFID tags is well established. Tags may permit a machine to accurately read information that is associated, assigned and/or affixed to an object. The information may be a unique number (e.g. a product code), characteristics (e.g. product features), or in the case of RFID real-time information from a sensor connected to the tag (e.g. temperature or pressure).

In the system 1, the drive-unit 20 is equipped with the tag reader 24 that is enabled to read one or more tags including the vessel tag 35 and the structure tag 15 when docked with and/or connected to the single-use vessel 30. The vessel tag 35 may be implemented as a 2D barcode (e.g. QR code) arranged visible through a hole or through an optical window, in particular through the reading area 16 in the support structure 10. The structure tag 15 may also be provided as a 2D barcode.

Usually, the drive-unit 20 is not powered when in storage or when in transport from one single-use mixing container to another. An operator may engage the drive-unit 20 with a single-use mixing container like the single-use vessel 30 and then plug in the drive-unit 20. Although the drive-unit 20 may be equipped with a battery to keep a control system active during transport, this is not required and may add cost and complexity. The tag reader 24 on the drive-unit 20 may be located such that the vessel tag 35 and structure tag 15 are in the field of view, namely the scan field 25, when the drive-unit 20 is fully engaged with and connected to the support structure 10.

Figure 6:
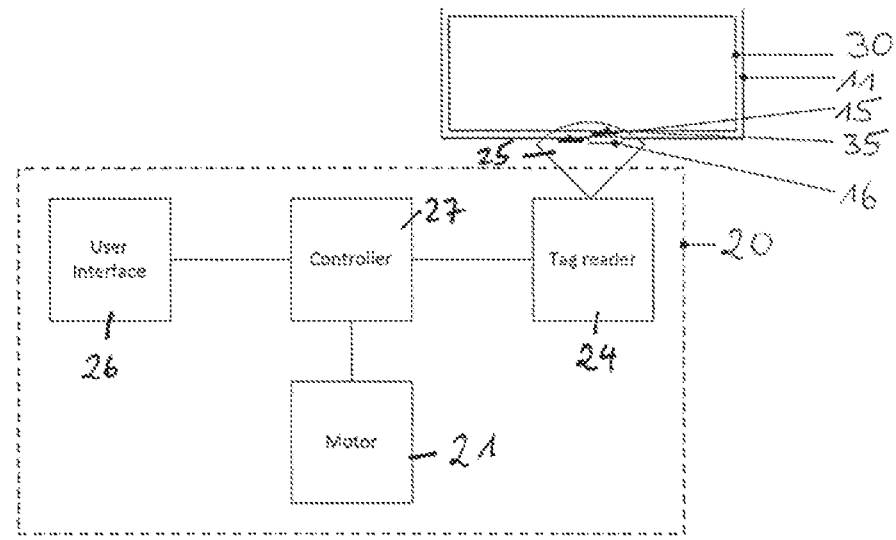
FIG. 6 a schematic diagram of some components of the system for receiving a single-use vessel.

FIG. 6 shows a schematic diagram of some components of a system 1 for receiving a single-use vessel 30. Therein, an exemplary arrangement of the features single-use bag 30, receiving section 11, structure tag 15, vessel tag 35, reading area 16, scan field 25, and tag reader 24 are shown once more in a schematic side view.

Furthermore, the drive-unit 20 is shown comprising a controller 27 connected to the tag reader 24, to the motor 21, and to the user interface 26 that may be implemented as a display as described above.

A tag information of the vessel tag 35 may be associated and/or include one or more attributes such as product code, product type, serial number, lot number, bag volume, information about ports and lines, sensor features, sensor calibration information, impeller characteristics, manufacturing date, irradiation date, expiration date, and manufacturer test results.

A tag information of the structure tag 15 may be associated and/or include one or more attributes such as product code, product type, serial number, intended bag volume, information about compatible ports and lines, portable/fixed, manufacturing date, and manufacturer test results.

The controller and/or control system 27 of the drive-unit 20 may make use of the available tag information in one or more of the following ways:

The control system 27 may check a compatibility of the single-use vessel 30 with the supporting structure 10 and/or the drive-unit 20. If the single-use vessel 30 is found to be incompatible, e.g., with the supporting structure 10, then the operator may be alerted and the drive-unit will not function and/or will not be powered until the problem is corrected.

The control system 27 may use a nominal volume of the single-use vessel 30 or of the support structure 10 to determine a suitable mixing speed range for the mixing device 31 of the single-use vessel 30, in particular of an impeller of the mixing device 31 that is contained within the vessel 30. For example, the control system 27 may have stored in its memory a lookup table which relates a nominal vessel volume to a recommended maximum speed.

The control system 27 may use a nominal volume of the single-use vessel 30 or at the support structure 10 to determine a suitable mixing duration for liquid-liquid or for powder-liquid blending. For example, the control system 27 may have stored in its memory a lookup table which relates a nominal vessel volume to a recommended time for liquid-liquid and powder-liquid blending.

Figure 7:
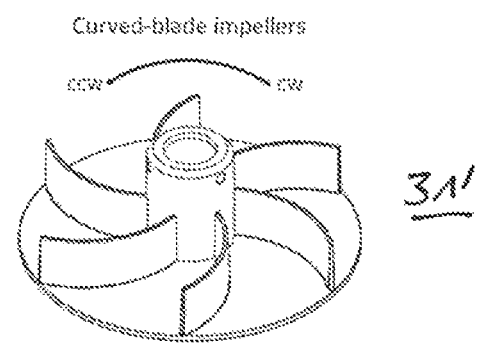
FIG. 7 a perspective view of an impeller contained in a single-use vessel.

The control system 27 may use impeller characteristics to determine a correct and/or preferred direction of rotation for the impeller. Some impellers (e.g. the impeller 31' as shown as a curved blade turbine in FIG. 7 in a perspective view) are best rotated in a specific direction to achieve efficient operation. For example, the impeller 31' may have a lower torque demand when rotated in a first direction, e.g. a counterclockwise direction ccw. The impeller 31' may have a higher torque demand when rotated in a second direction, e.g. a clockwise direction cw. The control system 27 may enforce proper rotation direction depending on the tag information of, e.g., the vessel tag 35.

The control system 27 may use a power supplied to the motor 21 and a nominal vessel volume from the vessel tag to calculate, monitor, and/or control power per unit volume (P/V), which may be a quantity of interest for scaling mixing performance.

The control system 27 may use impeller characteristics to determine an expected torque vs. speed curve for the impeller in the bag. The torque vs. speed curve may be stored on the vessel tag 35, on the structure tag 35, and/or in the drive-unit 20.

The control system 27 may use vessel feature information to determine whether the single-use vessel 30 has a powder port 32 (e.g. acanotier). If the vessel 30 has a powder port 32, the control system 27 may prompt an operator to take actions which are required for adding powder (e.g. open port, add powder, close port). If no powder port 32 present, then the control system 27 will not prompt the operator to take actions which are required for adding powder.

The control system 27 may use sensor information, e.g. from the sensor(s) 34 of the vessel 30, to determine whether a specific sensor (e.g. pH sensor) is present or not. If the sensor is present, then the control system 27 may prompt the operator to take specific actions, e.g. plug the sensor into a receptacle.

The control system 27 may use calibration information to transform a raw signal from a sensor 24 (e.g. millivolts) to an accurate measurement of a specific quantity (e.g. temperature).

The control system 27 may transmit vessel and/or structure information to a supervisory control and data acquisition (SCADA) system as part of the process record.

In other words, the controller 27 of the drive-unit 20 may control, power, and/or drive the system 1 depending on the tag information read out by the tag reader 24. In particular, the controller 27 may control the mixing direction, speed and duration of the contents of the vessel 30, reading out sensor signal(s) of the sensor(s) 24, etc. depending on the tag information.

LIST OF REFERENCE NUMERALS

1 System
10 support structure
11 receiving section
12 stand
13 roll
14 couple section
15 structure tag
16 reading area
20 drive-unit
21 motor
22 connector
23 roll
24 tag reader
25 scan field
26 user interface
27 controller
30 single-use vessel
31 mixing device
31' impeller
32 powder port
33 liquid port
34 sensor
35 vessel tag
ccw counterclockwise direction
cw clockwise direction

What is claimed is:

1. A system for receiving a single-use vessel that has a mixing device disposed at least partly within the single-use vessel, the system comprising:
a support structure configured to receive the single-use vessel, the support structure having a couple section disposed and configured so that at least part of the mixing device is accessible at the couple section when the single use vessel is received by the support structure, and
a drive-unit that is moveable relative to the support structure from a separated position where the drive unit is separated completely from the support structure and from the mixing device and an operating position where the drive unit is in the couple section and at a position to be connected to the mixing device of the single-use vessel in the support structure to power, to control, or to power and control the mixing device disposed at least partly within the single-use vessel for mixing of contents of the single-use vessel when the single-use vessel is arranged in the support structure,
wherein
the drive-unit comprises a tag reader that is movable with the drive unit and relative to the support structure so that, in the operating position, the tag reader is arranged in the couple section to read a vessel tag of the single-use vessel arranged in the support structure.

2. The system of claim 1, wherein the support structure comprises positioning means adapted to position the single-use vessel so that the vessel tag of the single-use vessel is arranged in a designated reading area of the support structure.

3. The system of claim 2, wherein the reading area of the support structure comprises a window substantially facing the drive-unit in the operating position.

4. The system of claim 2, wherein the tag reader of the drive-unit substantially faces the reading area of the support structure in the operating position.

5. The system of claim 1, wherein the support structure comprises a structure tag arranged to be readable by the tag reader when the drive-unit is in the operating position.

6. The system of claim 5, wherein the structure tag of the support structure is associated to tag information regarding at least one of the following:
- a product code,
- a product type,
- a serial number,
- an intended vessel volume,
- compatible ports
- compatible lines,
- portable or fixed,
- a manufacturing date, and
- manufacturer test results.

7. The system of claim 1, wherein the tag reader is adapted to determine tag information regarding at least one of the following:
- a product code,
- a product type,
- a serial number,
- a lot number,
- a vessel volume,
- ports of the single-use vessel,
- lines of the single-use vessel,
- a sensor feature,
- a sensor calibration information,
- characteristics of the mixing device,
- impeller characteristics of the mixing device,
- a manufacturing date,
- an irradiation date,
- an expiration date, and
- manufacturer test results from the vessel tag of the single-use vessel.

8. The system of claim 1, wherein the tag reader is adapted to read at least one of a QR code and an RFID tag.

9. The system of claim 1, further comprising a controller connected to the tag reader that is adapted to receive tag signals from the tag reader and that is further adapted to process said tag signals, thereby extracting tag information associated to at least one of the vessel tag and a structure tag of the support structure.

10. The system of claim 9, wherein the controller of the drive-unit is adapted to control the drive-unit depending on the extracted tag information.

11. The system of claim 1, wherein the drive-unit is arranged below the single-use vessel in the operating position.

12. The system of claim 1, wherein the drive-unit is mounted on rolls.

13. The system of claim 1, wherein the support structure includes a receiving section configured to receive the single-use vessel and a supporting structure that supports the receiving section above the couple section, the coupling section comprising a free space that is configured to accommodate the drive-unit in a position below the receiving section when the drive-unit is in the operating position.

14. The system of claim 1, wherein at least one of the support structure and the drive-unit comprises wheels configured to permit relative movement of at least one of the support structure and the drive-unit between the operating position and the separated position.

15. The system of claim 1, wherein at least one of the support structure and the drive-unit comprises wheels configured to permit relative movement of at least one of the support structure and the drive-unit between the operating position and the separated position.

16. A mixing system, comprising:
- a single-use vessel that has a mixing device disposed at least partly therein and that has a vessel tag thereon;
- a support structure removably supporting the single-use vessel, the support structure having a couple section disposed and configured so that so that at least part of the mixing device is accessible at the couple section; and
- a drive-unit that is moveable relative to the support structure from a separated position where the drive unit is separated completely from the support structure and from the mixing device and an operating position where the drive unit is connected to the mixing device of the single-use vessel in the support structure to power, to control, or to power and control the mixing device for mixing of contents of the single-use vessel, and a tag reader on the drive-unit so that, when the drive-unit is in the operating position, the tag reader is arranged to read the vessel tag of the single-use vessel arranged in the support structure.

* * * * *